United States Patent [19]

Martel et al.

[11] 4,401,673

[45] Aug. 30, 1983

[54] PESTICIDAL 3-(BUTA-1',3'-DIENYL)-CYCLOPROPANE-1-CARBOXYLIC ACID ESTERS

[75] Inventors: Jacques Martel, Bondy; Jean Tessier, Vincennes; Pierre Girault, Paris, all of France

[73] Assignee: Roussel Uclaf, Paris, France

[21] Appl. No.: 228,454

[22] Filed: Jan. 26, 1981

[30] Foreign Application Priority Data

Jan. 25, 1980 [FR] France ................. 80 01640

[51] Int. Cl.³ ............... A01N 53/00; C07D 213/57; C07C 69/743; C07C 121/75
[52] U.S. Cl. .............. 424/263; 260/465 D; 424/274; 424/282; 424/285; 424/304; 424/305; 546/330; 549/447; 549/485; 549/499; 549/513; 560/124
[58] Field of Search ........ 260/465 D; 560/124; 424/304, 263, 274, 282, 285, 305; 546/330; 549/447, 485, 499, 513

[56] References Cited

U.S. PATENT DOCUMENTS 3,954,814  5/1976  Mizutani et al. .............. 260/347.4

*Primary Examiner*—Dolph H. Torrence
*Attorney, Agent, or Firm*—Hammond & Littell, Weissenberger and Muserlian

[57] ABSTRACT

Novel 3-(buta-1',3'-dienyl)-cyclopropane-1-carboxylic acid compounds of the formula

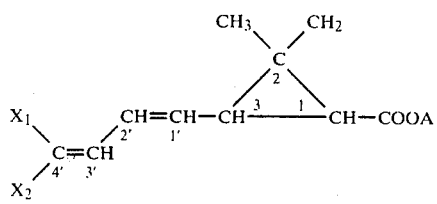

wherein $X_1$ and $X_2$ are individually a halogen and A is selected from the group consisting of (A) benzyl optionally substituted (B)

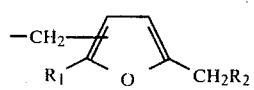

wherein $R_1$ is selected from the group consisting of hydrogen and $-CH_3$ and $R_2$ is selected from the group consisting of aryl and $-CH_2-C\equiv CH$, (C)

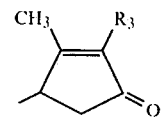

wherein $R_3$ is an aliphatic of 2 to 6 carbon atoms containing at least one carbon-carbon unsaturation, (D)

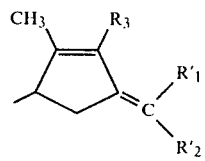

wherein $R'_1$ and $R'_2$ are individually selected from the group consisting of hydrogen, halogen, alkyl of 1 to 6 carbon atoms, aryl of 6 to 10 carbon atoms, alkoxycarbonyl of 2 to 5 carbon atoms and cyano and $R_3$ has the above definition, (E)

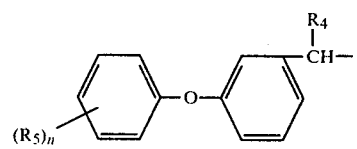

wherein $R_4$ is selected from the group consisting of hydrogen, $-CN$, $-CH_3$, $-CONH_2$, $-CSNH_2$ and $-C\equiv CH$, $R_5$ is selected from the group consisting of chlorine and $-CH_3$ and n is 0, 1 or 2, (F) α-cyano-3-phenoxy-benzyl, (G) α-cyano-3-pyridinyl-benzyl and (H)

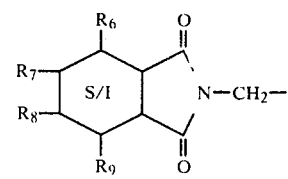

wherein $R_6$, $R_7$, $R_8$ and $R_9$ are individually selected from the group consisting of hydrogen, chlorine and $-CH_3$ and S/I indicates the ring may be aromatic or dihydro or tetrahydro useful for combatting insects, acariens and nematodes.

16 Claims, No Drawings

PESTICIDAL 3-(BUTA-1',3'-DIENYL)-CYCLOPROPANE-1-CARBOXYLIC ACID ESTERS

OBJECTS OF THE INVENTION

It is an object of the invention to provide the novel compounds of formula I and a novel process and novel intermediates for the preparation thereof.

It is another object of the invention to provide novel pesticidal compositions and to provide a novel method of combatting parasites of vegetables and warm-blooded animals.

These and other objects and advantages of the invention will become obvious from the following detailed description.

THE INVENTION

The novel compounds of the invention are 3-(buta-1',3'-dienyl)-cyclopropane-1-carboxylic acid compounds of all the possible stereoisomers or mixtures of stereoisomers of compounds of the formula

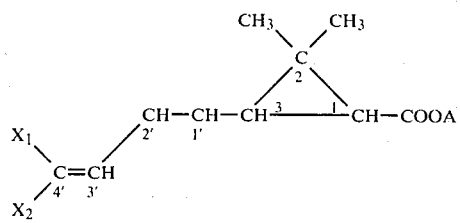

wherein $X_1$ and $X_2$ are individually a halogen and A is selected from the group consisting of (A) hydrogen, alkali metal, alkaline earth metal, —$NH_4$, copper, zinc and non-toxic, pharmaceutically acceptable organic amines, (B) alkyl of 1 to 18 carbon atoms, (C) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogen, (D)

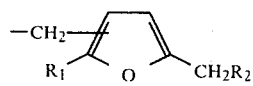

wherein $R_1$ is selected from the group consisting of hydrogen and —$CH_3$ and $R_2$ is selected from the group consisting of monocyclic aryl and —$CH_2$—C≡CH, (E)

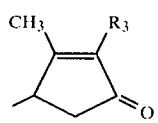

wherein $R_3$ is an aliphatic of 2 to 6 carbon atoms containing at least one carbon-carbon unsaturation, (F)

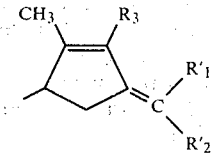

wherein $R_1'$ and $R_2'$ are individually selected from the group consisting of hydrogen, halogen, alkyl of 1 to 6 carbon atoms, aryl of 6 to 10 carbon atoms, alkoxycarbonyl of 2 to 5 carbon atoms and cyano and $R_3$ has the above definition, (G)

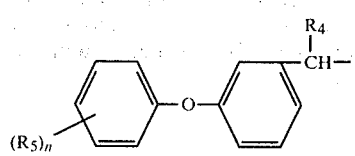

wherein $R_4$ is selected from the group consisting of hydrogen, —CN, —$CH_3$, —$CONH_2$, —$CSNH_2$ and —C≡CH, $R_5$ is selected from the group consisting of chlorine and —$CH_3$ and n is 0, 1 or 2, (H) α-cyano-3-phenoxy-benzyl, (I) α-cyano-3-pyridinyl-benzyl and (J)

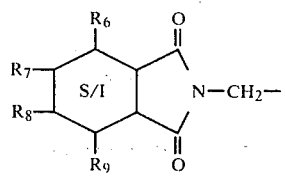

wherein $R_6$, $R_7$, $R_8$ and $R_9$ are individually selected from the group consisting of hydrogen, chlorine and —$CH_3$ and S/I indicates the ring may be aromatic or dihydro or tetrahydro.

Examples of $R_3$ are vinyl, propen-1-yl, buta-1,3-dienyl and buten-1-yl and examples of A are 5-benzyl-3-furyl-methyl, 3-phenoxy-benzyl, α-cyano-3-phenoxy-benzyl and α-cyano-ethynyl-3-phenoxy-benzyl. $X_1$ and $X_2$ are preferably chlorine, bromine or iodine.

The compounds of formula I can exist in a number of isomeric forms due to the two asymetric carbon atoms in the 1- and 3-positions of the cyclopropane ring and the possibility of E and Z isomers due to the 1',2'-double bond and when $X_1$ and $X_2$ are different, there is a possibility of E and Z isomers due to the 3',4'-double bond. Group A may also possess one or more asymetric centers. Preferably the acid moiety has the 1R, cis or 1R, trans structure.

Examples of group A are alkyl such as methyl, ethyl, isopropyl, n-propyl or n-butyl; benzyl substituted with one or more alkyl such as methyl or ethyl; benzyl substituted with one or more alkenyl such as vinyl, allyl, 2-methylallyl or isobutenyl; benzyl substituted with at least one alkenyloxy such as vinyloxy, allyloxy, 2-methylallyloxy or isobutenyloxy; benzyl substituted with at least one alkadienyl such as buta-1',3'-dienyl or pentadienyl; benzyl substituted with at least one halogen such as chlorine or bromine.

Preferred groups of compound of formula I are those wherein $X_1$ and $X_2$ are the same and are either bromine and chlorine and A is hydrogen or a salt of the said acid, especially the alkali metal, alkaline earth metal, copper, zinc or organic amine salts, those wherein A is alkyl or 1 to 4 carbon atoms, especially methyl, those wherein A is α-cyano-3-phenoxy-benzyl and those wherein A is 3-allyl-2-methyl-4-oxo-cyclopent-2en-1-yl.

The novel process of the invention for the preparation of the compounds of formula I comprises reacting a compound of the formula

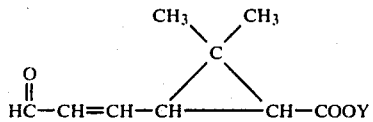

wherein Y is selected from the group consisting of hydrogen and alkyl of 1 to 18 carbon atoms in any one of its isomeric forms or mixtures thereof with a compound of the formula

wherein $X_1$, $X_2$ and $X_3$ all are bromine or chlorine or if two of the Xs are different are selected from the group consisting of bromine, chlorine and fluorine of the same atomic weight or increasing from $X_1$ to $X_3$ to obtain a compound of the formula

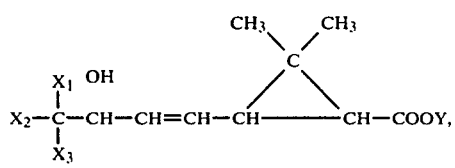

blocking the hydroxy group with an acid of the formula R—COOH or a functional derivatives thereof to obtain a compound of the formula

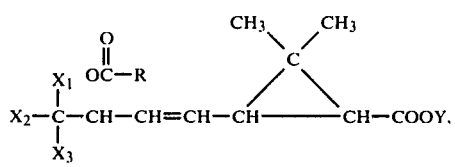

reacting the latter with a reducing agent and eliminating $X_3$ which is the substituent or one of the substituents with the greater atomic weight to obtain a compound of the formula

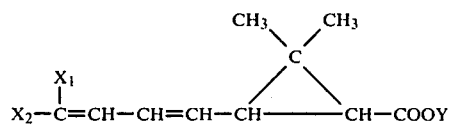

wherein $X_1$ and $X_2$ are both chlorine or bromine or are different and are selected from the group consisting of fluorine, bromine and chlorine and optionally, when Y is alkyl of 1 to 18 carbon atoms, subjecting the compound of formula $I_A$ to a saponification agent to obtain the compound of formula I when A is hydrogen or a salt thereof or optionally, when Y is alkyl of 1 to 18 carbon atoms or hydrogen or a functional derivative of the acid, reacting the compound of formula $I_A$ with an alcohol of the formula $A_1$-OH or a functional derivative thereof wherein $A_1$ has the definition of A except for hydrogen to obtain the corresponding compound of formula I.

In a preferred mode of the process of the invention, Y is alkyl and the hydroxyl of the compound of formula IV is blocked by acylation with an acid anhydride such as acetic anhydride or an acid halide such as acetyl chloride or acetyl bromide. The preferred reducing agent is zinc in the presence of acetic acid or a zinc-copper couple in the presence of an alcohol and the saponification agent is sodium hydroxide or potassium hydroxide. The preferred functional derivative of formula $I_A$ is the acid chloride but equally useful are the alkali metal salts such as the sodium and potassium salts and the alcohol derivative is preferably a halide such as the chloride or bromide.

In a variation of the process of the invention, the compound of formula II is subjected to the Wittig reaction with a compound of the formula

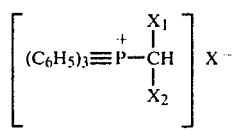

wherein $X_1$ and $X_2$ have the above definition and X is a halogen anion to obtain the corresponding compound of formula $1_A$ which, if desired, can then be treated as discussed above. The latter process is especially preferred for the compounds of formula II having the 1R, cis or 1R, trans structure. The Wittig reaction is effected in the presence of a strong base such as an alkali metal hydride, an alkali metal amide, an alkyllithium or alkali metal alcoholate, preferably sodium, potassium or lithium tert.-butylate.

The compounds of formula II are generally known and may be prepared by the process described by Elliott et al [J. Chem. Soc., Perkin 1, p. 2470]. (1R,cis) 2,2-dimethyl-3(3'-oxo-1'-propenyl)-cyclopropane-1-carboxylic acid is a novel intermediate product produced by the process of the invention. The compounds of formulae IV and V are also novel intermediate compounds produced by the process of the invention.

The novel compositions for the control of parasites of vegetable and warm-blooded animals are comprised of a parasiticidally effective amount of at least one compound of formula I and an inert carrier. The compositions may be in the form usually used in agrochemical industry, veterinary industry and in the animal feed industry. The compositions may also contain one or more other pesticidal agents and may be in the form of powders, granules, suspensions, emulsions, solutions, aerosol solutions, combustible strips, baits or other preparations classically used for these types of compounds.

The compositions may generally contain also a vehicle and/or a non-ionic surface active agent to ensure a uniform dispersion of the constituents of the mixtures. The vehicle may be a liquid such as water, alcohol, hydrocarbons or other organic solvents or a mineral, animal or vegetable oil or a powder such as talc, clays, silicates, kieselguhr or a combustible solid such as tabu powder or pyrethrum residue.

The compositions of the invention are useful for combatting insects, nematodes and parasitic acariens of vegetables or warm-blooded animals. The compositions are used as insecticides in the agricultural field to combat, for example, fleas, lepidolite larvae and coleopterons and are used at doses of 10 to 300 g of active material per hectare. The compositions are also useful to combat household insects such as houseflies, mosquitoes and beetles.

The compositions are also useful to combat vegetable acariens and parasitic nematodes. The compositions may be used to combat warm-blooded animals parasites such as ticks of the Boophilus species or Hyalomma, Amblyomma and Rhipicephalus species or to combat all types of scabies such as sarcoptic scabies, psoroptic scabies or chorioptic scabies.

The insecticidal compositions of the invention preferably contain 0.005 to 10% by weight of the active ingredient and the namatocidal compositions are preferably liquids containing 300 to 500 g/l of the active ingredient. For use as an acaricide, the compositions are preferably in the form of a wettable powder for foliar spraying containing 1 to 80% by weight of the active ingredient or as a liquid for foliar spraying containing 1 to 500 g/l of the active ingredient. The said compositions may also be in the form of powders for foliage powdering containing 0.05 to 3% by weight of the active ingredient. Generally, the nematocidal and acaricidal compositions are applied at a dose of 1 to 100 g of active material per hectare.

To increase the biological activity, the compositions of the invention may contain a classical synergist for these types of compounds such as piperonyl butoxide or 1-(2,5,8-trioxadodecyl)-2-propyl-4,5-methylenedioxybenzene and tropital or piperonyl-bis-2-(2'-n-butoxyethoxy)-ethyl acetal.

The compositions of the invention have an excellent general tolerance and are useful in human medicine and veterinary medicine both as a preventative or curative composition for combatting scabies or affections caused by ticks. The medicinal compositions may be externally administered such as by vaporization, baths or painting. The preferred verterinary method of administration is by painting of the dorsal spine by the so-called "pour-on" method although it may also be administered orally, rectally or parenterally.

When the compositions are to be used to combat animal parasites, the active products may be incorporated in alimentary compositions in association with a nutrive mixture adapted for the animal feed. The nutrive mixture will vary depending on the species of animal being treated and may contain cereals, sugars and grains, soy bean press cake, peanuts and turnsole, flour of animal origin such as fish flour, synthetic amino acids, mineral salts, vitamins and antioxidants.

The compositions of the invention may also be used as biocides or as increasing regulators.

The compounds of formula I of the invention wherein A is hydrogen or its salts or alkyl of 1 to 18 carbon atoms are not only biologically active but also are useful as intermediates for the synthesis of other biologically active compounds. The preferred biologically active compounds of formula I are those wherein A is other than hydrogen or its salts or alkyl of 1 to 18 carbon atoms.

The compounds of formula I also possess interesting organoleptic properties which make them useful as perfume agents. Particularly useful for this purpose are the compounds of formula I wherein A is alkyl of 1 to 4 carbon atoms, especially methyl, as they have a remarkable floral odor. Because of these interesting olfactory properties, the compounds of formula I are useful as odorants in perfumery to prepare odorant compositions to be used in perfume bases and the invention also includes perfume compositions containing at least one compound of formula I as an active principle.

The compounds of formula I are also useful to prepare hygenic articles such as soaps, shampoos, and talcum powders, to prepare detergent products such as wash powders or to prepare maintenance products such as waxes.

The novel method of combatting pests of vegetables and warm-blooded animals comprises contacting the pests with a pesticidal amount of at least one compound of formula I.

In the following examples there are described several preferred embodiments to illustrate the invention. However, it should be understood that the invention is not intended to be limited to the specific embodiments.

EXAMPLE 1

(1R,cis) 2,2-dimethyl-3-(4',4'-dichloro-buta-1',3'-dienyl)-cyclopropane-1-carboxylic acid

STEP A: (1R,cis) 2,2-dimethyl-3-(3'-oxo-1'-propenyl)-cyclopane-1-carboxylic acid A mixture of 180 g of 2-(bromoethyl)-1,3-dioxolane and 260 g of triphenylphosphine was heated at 80° C. for 36 hours and the mixture was cooled and filtered. The product was dissolved in methylene chloride and the solution was poured into 3000 ml of ether. The mixture was stirred and vacuum filtered and the product was empasted with ether to obtain 359 g of triphenyl-(1,3-dioxolan-2-yl)-phosphonium bromide melting at 206° C.

159.5 g of the said bromide were added portion-wise at 20° C. under an inert atmosphere to a mixture of 76.5 g of potassium tert.-butylate, 440 ml of heptane and 63.8 ml of tert.-butanol and after cooling the mixture to −10° C., a mixture of 44 g of (1R,5S) 6,6-dimethyl-4(R)-hydroxy-3-oxo-bicyclo [3-1-0] hexane-2-one in 180 ml of tetrahydrofuran was added. The mixture was held at −10° C. for one hour and 17 hours at room temperature and was then evaporated to dryness under reduced pressure. The residue was taken up in 1400 ml of 0.25 N sodium hydroxide solution and 320 ml of methylene chloride and the decanted aqueous phase was treated with activated carbon. 176 ml of tetrahydrofuran and 70 ml of concentrated hydrochloric acid were added to the mixture which was then stirred for 3½ hours at 20° C. The mixture was extracted with methylene chloride and the organic phase was washed with water, dried and evaporated to dryness. The residue was taken up in isopropyl ether and the mixture was stirred at 0° C. for 30 minutes and was vacuum filtered to obtain 23.7 g of (1R,cis) 2,2-dimethyl-3-(3'-oxo-1'-propenyl)-cyclopropane-carboxylic acid melting at 129° C.

STEP B: (1R,cis) 2,2-dimethyl-3-(4',4',4'-trichloro-3'-hydroxy-buta-1'-enyl)-cyclopropane-1-carboxylic acid A solution of 9.2 g of potassium methylate, 39 ml of butanol and 32 ml of tetrahydrofuran was added dropwise at −10° C. under an inert atmosphere to a mixture of 10 g of the product of Step A and 24 ml of chloroform and the mixture was stirred at −5° to 0° C. for 2 hours. The mixture was poured into 300 ml of a water-ice mixture and 13 ml of concentrated hydrochloric acid and the decanted aqueous phase was extracted with chloroform. The organic phase was washed with water, dried and evaporated to dryness under reduced pressure. The residue was taken up in petroleum ether (b.p.=60° to 80° C.) and was vacuum filtered to obtain 9.3 g of (1R,cis) 2,2-dimethyl-3-(4,40 ,4',4'-trichloro-3'-hydroxy-buta-1'-enyl)-cyclopropane-1-carboxylic acid melting at 138° C.

STEP C: (1R,cis) 2,2-dimethyl-3-(4',4',4'-trichloro-3'-acetoxy-buta-1-enyl)-cyclopropane-1-carboxylic acid A mixture of 8 g of the product of Step B, 22.5 ml of pyridine and 11.5 ml of acetic acid anhydride was stirred at room temperature for 4 hours and ice was added thereto with stirring. The mixture was poured into a mixture of 30 ml of concentrated hydrochloric acid and 150 ml of iced water. The mixture was extracted with chloroform and the organic phase was washed with water, dried, treated with activated carbon and evaporated to dryness under reduced pressure to obtain 9.56 g of (1R,cis) 2,2-dimethyl-3-(4',4',4'-trichloro-3'-acetoxy-buta-1-enyl)-cyclopropane-1-carboxylic acid as an oil which was used as is for the next step.

STEP D: (1R,cis) 2,2-dimethyl-3-(4',4'-dichloro-buta-1',3'-dienyl)-cyclopropane-1-carboxylic acid 5.65 g of powdered zinc were added with stirring to a mixture of 9.5 g of the product of Step C and 95 ml of acetic acid containing 10% of water and the mixture was stirred for 4 hours at about 35° C. The mixture was evaporated to dryness under reduced pressure and the residue was taken up in water. The solution was extracted with chloroform and the organic phase was washed with water, treated with activated carbon, dried and evaporated to dryness. The residue was washed with toluene to obtain 6.5 g of oil which was chromatographed over silica gel. Elution with a 3-1 petroleum ether (b.p.=40°-70° C.)-ether mixture yielded 2.75 g of (1R,cis) 2,2-dimethyl-3'-(4',4'-dichloro-buta-1',3'-dienyl)-cyclopropane-1-carboxylic acid.

NMR Spectrum (deuterochloroform)

Peaks at 1.225–1.3 ppm (hydrogens of methyls); at 1.66 to 2.08 ppm (hydrogens of cyclopropyl); at 6.17 to 6.58 ppm (ethylenic hydrogens).

EXAMPLE 2

Methyl (1R,trans) 2,2-dimethyl-3-(4',4'-dichloro-buta-1',3'-dienyl)-cyclopropane-1-carboxylate

STEP A: Methyl (1R,trans)2,2-dimethyl-3-(4',4',4'-trichloro-3'-hydroxy-buta-1-enyl)-cyclopropane-1-carboxylate A solution of 5.25 g of potassium methylate, 20 ml of tert.-butanol and 15 ml of tetrahydrofuran was added with stirring at −5° to −10° C. to a mixture of 11.6 g of methyl (1R,trans) 2,2-dimethyl-3-(3'-oxo-1'-propenyl)-cyclopropane-1-carboxylate (prepared by process of Elliott et al, J. Chem. Soc., 1975, p. 2470) in 15 ml of chloroform and the mixture was stirred for 2 hours at −5° C. and was then poured into a mixture of 100 ml of ice-water mixture and 7.5 ml of concentrated hydrochloric acid. The stirred mixture was decanted and the aqueous phase was extracted with chloroform. The combined organic phases were dried and evaporated to dryness at 50° C. under reduced pressure and the residue was crystallized from petroleum (b.p.=60°-80° C.) to obtain 12.2 g of methyl (1R,trans) 2,2-dimethyl-3-(4',4',4'-trichloro-3'-hydroxy-buta-1-enyl)-cyclopropane-1-carboxylate melting at ≈20°-25° C.

STEP B: Methyl (1R,trans) 2,2-dimethyl-3-(4',4',4'-trichloro-3'-acetoxy-buta-1-enyl)-cyclopropane-1-carboxylate A mixture of 12.2 g of the product of Step A, 33.5 ml of pyridine and 16.8 ml of acetic acid anhydride was stirred at room temperature for 4 hours and then 40 g of ice were added thereto. The mixture was stirred for 30 minutes and was then poured in a mixture of 60 g of ice-water and 39 ml of concentrated hydrochloric acid. The mixture was stirred for 10 minutes and was extracted with methylene chloride. The organic phase was washed and dried and evaporated to dryness at 50° C. under reduced pressure to obtain 11.8 g of methyl (1R,trans) 2,2-dimethyl-3-(4',4',4'-trichloro-3'-acetoxy-buta-1-enyl)-cyclopropane-1-carboxylate.

STEP C: Methyl (1R,trans) 2,2-dimethyl-3-(4',4'-dichloro-buta-1',3'-dienyl)-cyclopropane-1-carboxylate 6.73 g of powdered zinc were added to a mixture of 11.8 g of the product of Step B and 236 ml of acetic acid containing 10% water and the mixture was heated at 55° C. for 4 hours and was then cooled to 20° C. and filtered. The filtrate was evaporated to dryness at 60° C. under reduced pressure and the residue was taken up in a mixture of 125 ml of methylene chloride and 100 ml of water. The stirred mixture was decanted and the organic phase was washed with aqueous saturated sodium bicarbonate solution. The aqueous phase was extracted with methylene chloride and the combined organic phases were washed with water, dried and evaporated to dryness under reduced pressure to obtain 9 g of a residue. The latter was chromatographed over silica gel and was eluted with a 9-1cyclohexane-ethyl acetate mixture to obtain 4.3 g of methyl (1R,trans) 2,2-dimethyl-3-(4',4'-dichloro-buta-1',3'-dienyl)-cyclopropane-1-carboxylate as an oil.

NMR Spectrum (deuterochloroform)

Peaks at 1.18–1.28 ppm (hydrogens of geminal methyls); at 1.58–1.67 ppm (1-hydrogen of cyclopropyl); at 2 to 2.21 ppm (3-hydrogen of cyclopropyl); at 3.68 ppm (hydrogens of methyl of ester); at 5.3 to 5.18 ppm (1-ethylenic hydrogens of side chain); at 6.1 to 6.6 ppm (2- and 3-hydrogens of ethylenic side chain).

EXAMPLE 3

(1R,trans) 2,2-dimethyl-3-(4',4'-dichloro-buta-1',3'-dienyl)-cyclopropane-1-carboxylic acid A mixture of 4.3 g of the product of Example 2, 114 ml of methanol and 17.2 ml of 2 N sodium hydroxide solution was refluxed for 4 hours and was then evaporated to dryness at 50° C. under reduced pressure. The residue was taken up in 50 ml of water and the solution was extracted with ether. The aqueous phase was adjusted to a pH of 1 with 2 N hydrochloric acid and was extracted with ether. The organic phase was dried and was evaporated to dryness at 30° C. under reduced pressure. The residue was heated at 50° C. for one hour to obtain 3.8 g of (1R,trans) 2,2-dimethyl-3-(4',4'-dichloro-buta-1',3'-dienyl)-cyclopropane-1-carboxylic acid.

NMR Spectrum (deuterochloroform)

Peaks at 1.16–1.28 ppm (hydrogens of geminal methyls); at 1.56–1.65 ppm (1-hydrogen of cyclopropyl); at 2.02–2.11–2.15–2.24 ppm (3-hydrogen of cyclopropyl); at 5.3 to 5.8 ppm (1-hydrogen of ethylenic side chain); at 6.2 to 6.4 ppm (2- and 3-hydrogens of ethylenic side chain); at 11.3 ppm (OH).

EXAMPLE 4

(1R,cis) 2,2-dimethyl-3-(4', 4'-dibromo-buta-1',3'-dienyl)cyclopropane-1-carboxylic acid A mixture of 24 ml of tert.-butanol, 16 ml of heptane and 6.6 g of potassium tert.-butylate was heated to 75° C. under an inert atmosphere and then 14.7 g of dibromomethyl triphenyl phosphonium bromide were added at 20° C. to the mixture. After cooling the mixture to 0° C., 4 g of the product of Step A of Example 1 were added thereto and the mixture was stirred at 0° C. for one hour, was heated at 50° C. for one hour and was then evaporated to dryness under reduced pressure. The residue was taken up in 30 ml of N sodium hydroxide solution and 20 ml of methylene chloride and 96 ml of distilled water were added thereto. The decanted aqueous phase was washed with methylene chloride and the combined organic phases were stirred with 20 ml of 0.25 N sodium hydroxide solution. The combined aqueous phases were treated with activated carbon and 4 ml of concentrated hydrochloric acid were added thereto. The gummy product was dissolved in methylene chloride and the solution was evaporated to dryness at 40° C. under reduced pressure to obtain 5.68 g of an oil. The latter was chromatographed over silica gel and was eluted with a 3-1 petroleum ether (b.p.=40° to 70° C.)-ether mixture to obtain 3 g of (1R,cis) 2,2-dimethyl-3-(4',4'-dibromo-buta-1',3'-dienyl)-cyclopropane-1-carboxylic acid.

NMR Spectrum (deuterochloroform)

Peaks at 1.23–1.3 ppm (hydrogens of geminal methyls); at 1.75 to 2.33 ppm (hydrogens of cyclopropyl); at 6.2 to 6.4 ppm and 6.9 to 7.1 ppm (ethylenic hydrogens).

EXAMPLE 5

Methyl (1R,trans) 2,2-dimethyl-3-(4',4'-dibromo-buta-1',3'-dienyl)-cyclopropane-1-carboxylate 9.74 g of potassium tert.-butylate and then 7.95 ml of tert.-butanol were added with stirring under an inert atmosphere at 20° C. to 100 ml of heptane and then 43.5 g of dibromomethyl triphenyl phosphonium bromide were slowly added thereto with stirring. The mixture was cooled to −10° C. and a solution of 12.8 g of methyl (1R,trans) 2,2-dimethyl-3-(3'-oxo-1'-propenyl)-cyclopropane-1-carboxylate in 40 ml of tetrahydrofuran was added to the mixture which was then stirred at −10° C. for one hour and at room temperature for 2 hours. The mixture was evaporated to dryness under reduced pressure and the residue was taken up in ice-water mixture. The mixture was extracted with methylene chloride and the organic phase was washed with an aqueous saturated monosodium phosphate solution, was dried and evaporated to dryness under reduced pressure. The residue was chromatographed over silica gel and was eluted with methylene chloride. Evaporation to dryness yielded 19.8 g of methyl (1R,trans) 2,2-dimethyl-3-(4',4'-dibromo-buta-1',3'-dienyl)-cyclopropane-1-carboxylate with a refractive index of $[n]_D^{23} = 1.561$.

NMR Spectrum (deuterochloroform)

Peaks at 1.15–1.25 ppm (hydrogens of geminal methyls); at 1.58–1.675 ppm (1-hydrogen of cyclopropyl); at 3.7 ppm (hydrogens of methyl of ester); at 1.99–2.08 ppm and 2.12–2.21 ppm (3-hydrogen of cyclopropyl); at 5.4–5.5 ppm and 5.6–5.8 ppm (1-hydrogen of ethylenic chain); at 6.0–6.2 ppm and 6.3–6.5 ppm (2-hydrogen of ethylenic side chain); at 6.8–7.0 ppm (3-hydrogen of ethylenic chain).

EXAMPLE 6

(1R,trans) 2,2-dimethyl-3-(4',4'-dibromo-buta-1',3'-dienyl)-cyclopropane-1-carboxylic acid Using the procedure of Example 3, 14 g of the product of Example 5 were reacted and the product was extracted with isopropyl ether. The residue was chromatographed over silica gel and was eluted with a 9-1 methylene chloride-ethyl acetate mixture to obtain 6.62 of (1R,trans) 2,2-dimethyl-3-(4',4'-dibromo-buta-1',3'-dienyl)-cyclopropane-1-carboxylic acid.

NMR Spectrum (deuterochloroform)

Peaks at 1.3–1.32 ppm (hydrogens of geminal methyls); at 1.6–1.68 ppm (1-hydrogen of cyclopropyl); at 2 to 2.25 ppm (3-hydrogen of cyclopropyl); at 5.4 to 5.8 ppm (1-hydrogen of ethylenic chain); at 6.1–6.3 ppm and 6.3–6.5 ppm (2-hydrogen of ethylenic chain); at 6.8–7.0 ppm (3-hydrogen of ethylenic chain).

EXAMPLE 7

(S)α-cyano-3-phenoxy-benzyl (1R,cis) 2,2-dimethyl-3-(4',4'-dichloro-buta-1',3'-dienyl)-cyclopropane-1-carboxylate STEP A: (1R,cis) 2,2-dimethyl-3-(4',4'-dichloro-buta-1',3'-dienyl)-cyclopropane-1-carboxylic acid chloride A mixture of 2,75 g of (1R,cis) 2,2-dimethyl-3-(4',4'-dichloro-buta-1',3'-dienyl)-cyclopropane-1-carboxylic acid, 28 ml of petroleum ether (b.p.=40°-70° C.) and 8.25 ml of thionyl chloride was refluxed for 4 hours and was evaporated to dryness at 35° C. under reduced pressure to obtain 2.91 g of (1R, cis) 2,2-dimethyl-3-(4',4'-dichloro-buta-1',3'-dienyl)-cyclopropane-1-carboxylic acid chloride.

STEP B: (S)α-cyano-3-phenoxy-benzyl (1R,cis) 2,2-dimethyl-3-(4',4'-dichloro-buta-1',3'-dienyl)-cyclopropane-1-carboxylate A mixture of 4.44 ml of pyridine and 9 ml of benzene was added dropwise at 15° C. to a mixture of the product of Step A, 30 ml of benzene and 2.7 g of (S)α-cyano-3-phenoxybenzyl alcohol and the mixture was stirred at room temperature for 17 hours and was poured into 100 ml of 2N hydrochloric acid. The mixture was stirred and the decanted organic phase was washed with water, treated with activated carbon, dried and evaporated to dryness under reduced pressure to obtain 4.87 g of residue. The latter was chromatographed over silica gel and was eluted with a 1-1 hexane-isopropyl ether mixture to obtain 1.5 g of (S)α-cyano-3-phenoxy-benzyl (1R,cis) 2,2-dimethyl-3-(4',4'-dichloro-buta-1',3'-dienyl)cyclopropane-1-carboxylate melting at 65° C. and having a specific rotation of $[\alpha]_D^{20} = +53° \pm 2.5°$ (c=0.5% in benzene).

NMR Spectrum (deuterochloroform)

Peaks at 1.23 ppm (hydrogens of geminal methyls); at 1.77 to 2.2 ppm (hydrogens of cyclopropyl); at 5.8 to 6.7 ppm (ethylenic hydrogens); at 6.5 ppm (hydrogen on carbon attached to —CN); at 7 to 7.6 ppm (aromatic hydrocarbons).

EXAMPLE 8

(R,S)α-cyano-3-phenoxy-benzyl (1R,trans) 2,2-dimethyl-3-(4',4'-dichloro-buta-1',3'-dienyl)-cyclopropane-1-carboxylate Using the procedure of Step A of Example 7, 2.32 g of the product of Example 3 were reacted to obtain 2.5 g of (1R,trans) 2,2-dimethyl-3-(4',4'-dichloro-buta-1',3'-dienyl)-cyclopropane-1-carboxylic acid chloride which was then reacted by the procedure of Step B of Example 7 with 2.3 g of (R,S)α-cyano-3-phenoxy-benzyl alcohol to obtain 4.90 g of raw product. The latter was chromatographed over silica gel and was eluted with a 3-1 petroleum ether (b.p.=40°-70° C.)-ether mixture to obtain 2.46 g of (R,S)α-cyano-3-phenoxy-benzyl (1R,trans) 2,2-dimethyl-3-(4',4'-dichloro-buta-1',3'-dienyl)-cyclopropane-1-carboxylate with a specific rotation of $[\alpha]_D^{20} = -25.6° \pm 2.5°$ (c=0.6% in benzene).

NMR Spectrum (deuterochloroform)

1.17-1.2-1.3 ppm (hydrogens of geminal methyls); at 1.55 to 1.72 ppm (1-hydrogen of cyclopropyl); at 2 to 2.33 ppm (3-hydrogen of cyclopropyl); at 6.33 ppm (hydrogen on carbon attached to —CN and 2- and 3-hydrogens of ethylenic chain); at 5.3 to 5.8 ppm (1-hydrogen of ethylenic chain); at 6.9 to 7.7 ppm (aromatic hydrogens).

EXAMPLE 9

(S)α-cyano-3-phenoxy-benzyl (1R, trans) 2,2-dimethyl-3-(4',4'-dichloro-buta-1',3'-dienyl)-cyclopropane-1-carboxylate Using the procedure of Step B of Example 7, 1.4 g of (1R, trans) 2,2-dimethyl-3-(4',4'-dichloro-buta-1',3'-dienyl)-cyclopropane-1-carboxylic acid chloride and 1.35 g of (S)α-cyano-3-phenoxy-benzyl alcohol were reacted to obtain 2.54 g of an oil product. The latter was chromatographed over silica gel and was eluted with an 85-15 cyclohexane-ethyl acetate mixture. The 1.86 g of product was crystallized from petroleum ether (b.p.=40°-70° C.) to obtain 1.3 g of (S)α-cyano-3-phenoxy-benzyl (1R, trans) 2,2-dimethyl-3-(4',4'-dichloro-buta-1',3'-dienyl)-cyclopropane-1-carboxylate melting at 78° C. and having a specific rotation of $[\alpha]_D^{20} = +6° \pm 2°$ (c=0.6% in benzene).

NMR Spectrum (deuterochloroform)

Peaks at 1.17-1.23 ppm (hydrogens of geminal methyls); at 1.66-1.75 ppm (1-hydrogen of cyclopropyl); at 2.1-2.19-2.24-2.33 ppm (3-hydrogen of cyclopropyl); at 5.2 to 5.8 ppm (3-hydrogen of ethylenic chain); at 6.2 to 6.6 ppm (1- and 2-hydrogens of ethylenic chain); at 6.3 to 6.5 ppm (hydrogen on carbon attached to —CN); at 7.0 to 7.6 ppm (aromatic hydrogens).

EXAMPLE 10

(S)α-cyano-3-phenoxy-benzyl (1R,cis) 2,2-dimethyl-3-(4',4'-dibromo-buta-1',3'-dienyl)-cyclopropane-1-carboxylate Using the procedure of Step A of Example 7, 7 g of (1R,cis) 2,2-dimethyl-3-(4',4'-dibromo-buta-1',3'-dienyl)-cyclopropane-1-carboxylic acid were reacted to obtain 7.6 g of (1R,cis) 2,2-dimethyl-3-(4',4'-dibromo-buta-1',3'-dienyl)-cyclopropane-1-carboxylic acid chloride which was reacted with 2.9 g of (S)α-cyano-3-phenoxy-benzyl alcohol by the procedure of Step B of Example 7 to obtain 5.83 g of the product. The latter was chromatographed over silica gel and was eluted with a 3-1 petroleum ether-ether mixture to obtain 1.61 g of (S)α-cyano-3-phenoxy-benzyl (1R,cis) 2,2-dimethyl-3-(4',4'-dibromo-buta-1',3'-dienyl)-cyclopropane-1-carboxylate with a specific rotation of $[\alpha]_D^{20} = +46.3° \pm 2°$ (c=0.4% in benzene).

NMR Spectrum (deuterochloroform)

Peaks at 1.22–1.23 ppm (hydrogens of geminal methyls); at 6.4 ppm (hydrogen on carbon attached to —CN); at 6.2 to 6.5 ppm (ethylenic hydrogens); at 6.9 to 7.7 ppm (aromatic hydrogens).

EXAMPLE 11

(R,S)α-cyano-3-phenoxy-benzyl (1R,trans) 2,2-dimethyl-3-(4',4'-dibromo-buta-1',3'-dienyl)-cyclopropane-1-carboxylate Using the procedure of Step A of Example 7, 1.8 g of (1R,trans) 2,2-dimethyl-3-(4',4'-dibromo-buta-1',3'-dienyl)-cyclopropane-1-carboxylic acid were reacted to obtain 1.9 g of (1R,trans) 2,2-dimethyl-3-(4',4'-dibromo-buta-1',3'-dienyl)-cyclopropane-1-carboxylic acid chloride which was then reacted with 1.4 g of (R,S)α-cyano-3-phenoxy-benzyl alcohol by the procedure of Step B of Example 7 to obtain 2.7 g of raw product. The latter was chromatographed over silica gel and was eluted with an 8-2 hexane-isopropyl ether mixture to obtain 1.33 g of (R,S)-α-cyano-3-phenoxy-benzyl (1R,trans) 2,2-dimethyl-3-(4',4'-dibromo-buta-1',3'-dienyl)-cyclopropane-1-carboxylate with a specific rotation or $[\alpha]_D^{20} = -14° \pm 2.5$ (c=0.5% in benzene).

NMR Spectrum (deuterochloroform)

Peaks at 1.18–1.23 ppm (hydrogens of geminal methyls of S product); at 1.23–1.32 ppm (hydrogens of geminal methyls of R product); at 1.65 to 1.75 ppm and 2.05 to 2.38 ppm (hydrogens of cyclopropyl); at 6.9 to 7.1 ppm (resolved 3-hydrogen of ethylenic chain); at 5.4 to 5.9 ppm (1-hydrogen of ethylenic chain); at 6.1 to 6.6 ppm (resolved 2-hydrogen of ethylenic chain); at 6.4 ppm (hydrogen of carbon attached to —CN); at 6.9 to 7.6 ppm (aromatic hydrogens).

EXAMPLE 12

(S)α-cyano-3-phenoxy-benzyl (1R, trans) 2,2-dimethyl-3-(4',4'-dibromo-buta-1',3'-dienyl)-cyclopropane-1-carboxylate Using the procedure of Step A of Example 7, 1.9 g of (1R, trans) 2,2-dimethyl-3-(4',4'-dibromo-buta-1',3'-dienyl)-cyclopropane-1-carboxylic acid chloride and 6.11 g of (S)α-cyano-3-phenoxy-benzyl alcohol were stirred for 17 hours at 20° C. and the mixture was poured into 200 ml of water with stirring. The decanted aqueous phase was extracted with benzene and the organic phase was washed with 0.1 N hydrochloric acid and then with water, was dried and evaporated to dryness under reduced pressure to obtain 15.4 g of raw product. The latter was chromatographed twice over silica gel and was eluted first with a 9-1 hexane-ethyl acetate mixture and then with an 8-2 hexane-isopropyl ether mixture to obtain 4.4 g of product which was crystallized from a 1-1 hexane-isopropyl ether mixture to obtain 2.2 g of (S)α-cyano-3-phenoxy-benzyl (1R,trans) 2,2-dimethyl-3-(4',4'-dibromo-buta-1',3'-dienyl)-cyclopropane-1-carboxylate melting at 110° C. and having a specific rotation of $[\alpha]_D^{20} = +116° \pm 1°$ (c=1% in benzene).

NMR Spectrum (deuterochloroform)

Peaks at 1.2–1.16 ppm (hydrogens of geminal methyls); at 2.1 to 2.3 ppm (3-hydrogen of cyclopropyl); at 1.66–1.75 ppm (1-hydrogen of cyclopropyl); at 5.4 to 5.8 ppm (1-hydrogen of ethylenic chain); at 6.1 to 6.5 ppm (2-hydrogen of ethylenic chain); at 6.8–7 ppm (3-hydrogen of ethylenic chain); at 6.4 ppm (hydrogen on carbon attached to —CN) at 6.9 to 7.6 ppm (aromatic hydrogens).

EXAMPLE 13

(S) 3-allyl-2-methyl-4-oxo-cyclopent-2-en-1-yl (1R,cis) 2,2-dimethyl-3-(4',4'-dichloro-buta-1',3'-dienyl)-cyclopropane-1-carboxylate Using the procedure of Example 7, 2.5 g of (1R, cis) 2,2-dimethyl-3-(4',4'-dichloro-buta-1',3'-dienyl)-cyclopropane-1-carboxylic acid were reacted to form the corresponding acid chloride which was then reacted with 1.8 g of (S) 3-allyl-1-hydroxy-2-methyl-4-oxo-cyclopent-2-ene to obtain 3.23 g of raw product. The latter was chromatographed over silica gel and was eluted with a 9-1 hexane-ethyl acetate mixture to obtain 600 mg of pure (S) 3-allyl-2-methyl-4-oxo-cyclopent-2-en-1-yl (1R,cis) 2,2-dimethyl-3-(4',4'-dichloro-buta-1',3'-dienyl)-cyclopropane-1-carboxylate with a specific rotation of $[\alpha]_D^{20} = +14° \pm 2°$ (c=0.4% in benzene).

NMR Spectrum (deuterochloroform)

Peaks at 1.22–1.28 ppm (hydrogens of geminal methyls); at 2 ppm (hydrogens of methyl of allethrolone); 2.93–3.0 ppm (1-hydrogens of allyl); at 4.7 to 5.2 ppm (3-hydrogens of allyl); at 5.6–5.7 ppm (hydrogen on carbon attached to —CN); at 5.4 to 6.3 ppm (2-hydrogen of allyl); at 6 to 6.5 ppm (3-hydrogens of ethylenic chain).

EXAMPLE 14

(S) 3-allyl-2-methyl-4-oxo-cyclopent-2-en-1-yl (1R, trans) 2,2-dimethyl-3-(4',4'-dichloro-buta-1',3'-dienyl)-cyclopropane-1-carboxylate Using the procedure of Example 7, 1.53 g of (1R, trans) 2,2-dimethyl-3-(4',4'-dichloro-buta-1',3'-dienyl)-cyclopropane-1-carboxylic acid were reacted to form the corresponding acid chloride which was reacted with 1.07 g of (S) 3-allyl-1-hydroxy-2-methyl-4-oxo-cyclopent-2ene to obtain 2.17 g of raw product. The latter was chromatographed over silica gel and was eluted with a 9-1 benzene-ethyl acetate mixture to obtain 850 mg of pure (S) 3-allyl-2-methyl-4-oxo-cyclopent-2-en-1-yl (1R, trans) 2,2-dimethyl-3-(4',4'-dichloro-buta-1',3'-dienyl)-cyclopropane-1-carboxylate having a refractive index of $n_D^{23.5} = 1.5539$ and a specific rotation of $[\alpha]_D^{20} = -76° \pm 2.5°$ (c=0.4% in benzene).

NMR Spectrum (deuterochloroform)

Peaks at 1.17–1.25 ppm (hydrogens of geminal methyls); at 2.0 ppm (hydrogens of methyl of allethrolone); at 1.6–1.69 ppm (1-hydrogen of cyclopropyl); at 4.7 to 5.2 ppm (3-hydrogens of allyl); at 5.3 to 6.2 ppm (2-hydrogen of allyl and 1-hydrogen of ethylenic chain); at 6.2 to 6.5 ppm (2- and 3-hydrogens of ethylenic chain).

EXAMPLE 15

(S) 3-allyl-2-methyl-4-oxo-cyclopent-2-en-1-yl (1R,trans) 2,2-dimethyl-3-(4',4'-dibromo-buta-1',3'-dienyl)-cyclopropane-1-carboxylate Using the procedure of Example 7, 2.0 g of (1R, trans) 2,2-dimethyl-3-(4',4'-dibromo-buta-1',3'-dienyl)-cyclopropane-1-carboxylic acid were reacted to obtain the corresponding acid chloride which was reacted with 1 g of 3-allyl-1-hydroxy-2-methyl-4-oxo-cyclopent-2-ene to obtain 2.5 g of raw product. The latter was chromatogrphed over silica gel and was eluted with an 8-2 hexane-isopropyl ether mixture to obtain 1.5 g of pure (S) 3-allyl-2-methyl-4-oxo-cyclopent-2-en-1-yl (1R,trans) 2,2-dimethyl-3-(4',4'-dibromo-buta-1',3'-dienyl)-cyclopropane-1-carboxylate with a specific rotation of $[\alpha]_D^{20} = -55.5° \pm 3°$ (c=0.3% in benzene).

NMR Spectrum (deuterochloroform)

Peaks at 1.2–1.28 ppm (hydrogens of geminal methyls); at 1.62–1.71 ppm (1-hydrogen of cyclopropyl); at 2.03 ppm (hydrogens of methyl of allethrolone); at 4.8–5.2 ppm (3-hydrogens of allyl; at 5.4 to 6.5 ppm (2-hydrogen of allyl); at 6.9–7.0 ppm (3-hydrogen of ethylenic chain); at 6.1 to 6.5 ppm (2-hydrogen of ethylenic chain); at 5.43 to 5.83 ppm (1-hydrogen of ethylenic chain).

EXAMPLE 16

(S) 3-allyl-2-methyl-4-oxo-cyclopent-2-en-1-yl (1R,cis) 2,2-dimethyl-3-(4',4'-dibromo-buta-1',3'-dienyl)-cyclopropane-1-carboxylate Using the procedure of Example 7, 6.2 g of (1R,cis) 2,2-dimethyl-3-(4',4'-dibromo-buta-1',3'-dienyl)-cyclopropane-1-carboxylic acid were reacted to obtain the corresponding acid chloride which was then reacted with 0.98 g of (S) 3-allyl-1-hydroxy-2-methyl-4-oxo-cyclopent-2-ene to obtain 2.2 g of raw product. The latter was chromatographed over silica gel and was eluted with an 8-2 hexane-isopropyl ether mixture to obtain 760 mg of (S) 3-allyl-2-methyl-4-oxo-cyclopent-2-en-1-yl (1R,cis) 2,2-dimethyl-3-(4',4'-dibromo-buta-1',3'-dienyl)-cyclopropane-1-carboxylate with a specific rotation of $[\alpha]_D^{20} = +1.25° \pm 1°$ (c=1.5% in benzene).

NMR Spectrum (deuterochloroform)

Peaks at 1.22–1.28 ppm (hydrogens of geminal methyls); at 2.0 ppm (hydrogens of methyl of allethrolone); at 4.8 to 5.2 ppm (3-hydrogens of allyl); at 5.7 ppm (1-hydrogen of allethrolone); at 5.5 to 7.1 ppm (hydrogens of ethylenic chain).

EXAMPLE 17

(1R,cis,ΔZ)
2,2-dimethyl-3-(4',4'-dibromo-buta-1',3'-dienyl)-cyclopropane-1-carboxylic acid STEP A: Tert.-butyl (1R, cis ΔZ) 2,2-dimethyl-3-(2'-formylethenyl)-cyclopropane-1-carboxylate A few crystals of p-toluene sulfonic acid were added to a mixture of 3.4 g of tert.-butyl (1R, cis) 2,2-dimethyl-3-(3',3'-diethoxy-prop-1-en-1-yl)-cyclopropane-carboxylate [Bestman et al, Angew. Chem. Int., Vol. 18 (1979), No. 9], 5 ml of water and 20 ml of acetone cooled to 0° to 5° C. and the mixture was stirred for 45 minutes at 0° to 5° C. and was then poured into an iced aqueous saturated sodium bicarbonate solution. The mixture was extracted with pentane and the organic phase was dried and evaporated to dryness to obtain 2.42 g of tert.-butyl (1R, cis, ΔZ) 2,2-dimethyl-3-(2'-formylethenyl)-cyclopropane-1-carboxylate.

NMR Spectrum (deuterochloroform)

Peaks at 1.28–1.33 ppm (geminal methyls); at 2.47–2.78 ppm (3-hydrogens); at 1.87–2.01 ppm (1-hydrogen); at 1.45 ppm (hydrogens of tert.-butyl); at 6.85–7.3 ppm (1'-hydrogen); at 5.93–6.06 ppm and 6.13–6.27 ppm (2'-hydrogen); at 10.1–10.2 ppm (3'-hydrogen).

STEP B: Tert.-butyl (1R, cis, ΔZ) 2,2-dimethyl-3-(4',4'-dibromo-buta-1',3'-dienyl)-cyclopropane-1-carboxylate A mixture of 3 ml of heptane, 4.5 ml of tert.-butanol and 0.28 g of lithium tert.-butylate was stirred for 15 minutes at 20° C. and then 2.27 g of dibromomethyl triphenyl phosphonium bromide were added thereto. The mixture was stirred at 20° C. for one hour and then was cooled to −60° C. after which a solution of 0.64 g of the product of Step A in 6 ml of heptane was added dropwise thereto. The temperature was allowed to rise to 0° C. and the mixture was stirred at 0° C. for 30 minutes and was then poured into a mixture of 60 ml of ice water and 60 ml of isopropyl ether. The decanted organic phase was dried, treated with activated carbon and evaporated to dryness. The residue was taken up in isopropyl ether and the solution was filtered. The filtrate was evaporated to dryness and the 1.48 g of residue was chromatographed over silica gel. Elution with a 95-5 hexane-isopropyl ether mixture yielded 0.53 g of tert.-butyl (1R, cis, ΔZ) 2,2-dimethyl-3-(4',4'-dibromo-buta-1',3'-dienyl)-cyclopropane-1-carboxylate.

STEP C: (1R,cis,ΔZ) 2,2-dimethyl-3-(4',4'-dibromo-buta-1',3'-dienyl)-cyclopropane-1-carboxylic acid A mixture of 0.48 g of the product of Step B, 5 ml of toluene and 0.030 g of p-toluene sulfonic acid was refluxed for 15 minutes and was then evaporated to dryness to obtain 0.5 g ((1R,cis,ΔZ) 2,2-dimethyl-3-(4',4'-dibromo-buta-1',3'-dienyl)-cyclopropane-1-carboxylic acid which was used as is for Example 18.

EXAMPLE 18

(S)α-cyano-3-phenoxy-benzyl (1R,cis,ΔZ) 2,2-dimethyl-3-(4',4'-dibromo-buta-1',3'-dienyl)-cyclopropane-1-carboxylate A mixture of 0.42 g of the product of Example 17, 2 ml of methylene chloride and 0.04 g of dimethylaminopyridine was stirred for 10 minutes and then cooled to 0° C. after which a mixture of 0.27 g of dicyclohexylcarbodiimide and 2 ml of methylene chloride was added dropwise thereto. The suspension was stirred for 15 minutes at 0° C. and then 0.34 g of (S)α-cyano-3-phenoxy-benzyl alcohol in 3 ml of methylene chloride were added thereto. The temperature was allowed to rise to 20° C. and the mixture was stirred at 20° C. for one hour and was filtered. The filtrate was evaporated to dryness and the residue was chromatographed over silica gel. Elution with an 8-2 hexane-isopropyl ether mixture yielded 0.57 g of (S)α-cyano-3-phenoxy-benzyl (1R,cis,ΔZ) 2,2-dimethyl-3-(4',4'-dibromo-buta-1',3'-dienyl)-cyclopropane-1-carboxylate.

IR Spectrum (chloroform)

Absorption at 1743 $cm^{-1}$ (ester carbonyl); at 1590–1490 $cm^{-1}$ (aromatic C=C); at 1390–1380 $cm^{-1}$ (gem dimethyls).

NMR Spectrum (deuterochloroform)

Peaks at 6.83 to 7.6 ppm (3'-hydrogens of ethylenic chain and aromatics); at 5.66 to 6.5 ppm (1' and 2'-hydrogens); at 6.41 ppm (hydrogen on carbon attached to −CN); at 1.23 ppm (geminal methyls).

EXAMPLE 19

An homogenous emulsifiable concentrate was prepared containing 0.25 g of the product of Example 7, 1 g of piperonyl butoxide, 0.25 g of Tween 80, 0.1 g of Topanol A and 98.4 g of water.

Another homogenous emulsifiable concentrate was prepared containing 0.015 g of the product of Example 7, 0.5 g of piperonyl butoxide, 0.1 g of Topanol A and 99.385 g of xylene.

An emulsifiable concentrate was prepared by homogenously mixing 1.5 g of the product of Example 7, 20 g of Tween 80, 0.1 g of Topanol A and 78.4 g of xylene.

A fumigant composition was prepared by homogenously mixing 0.25 g of the product of Example 7, 25 g of tabu powder, 40 g of powdered cedar needles, 33.75 g of pine sawdust, 0.5 g of vert brillant and 0.5 g of p-nitrophenol.

INSECTICIDAL ACTIVITY

The insecticidal activity was determined with larvae of Epilachna Varivestris to determine the $DL_{50}$, the dose at which 50% were killed, and the results are reported in the following Table.

TABLE

| Compound of Example | $DL_{50}$ in ng per insect |
|---|---|
| 7 | 1.8 |
| 10 | 1.9 |
| 12 | 2.9 |

The results of the test show that the tested compounds have a strong insecticidal activity against Epilachna Varivestris.

Various modifications of the products and methods of the invention may be made without departing from the spirit or scope thereof and it is to be understood that the invention is intended to be limited only as defined in the appended claims.

What we claim is:

1. A compound selected from the group consisting of 3-(buta-1',3'-dienyl)-cyclopropane-1-carboxylic acid compounds of all the possible stereoisomers or mixtures of stereoisomers of compounds of the formula

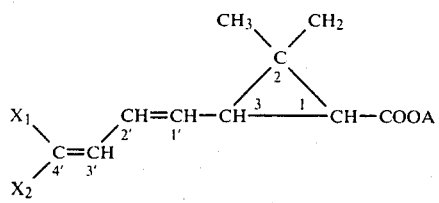

wherein $X_1$ and $X_2$ are individually a halogen and A is selected from the group consisting of (A) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogen, (B)

wherein $R_1$ is selected from the group consisting of hydrogen and —$CH_3$ and $R_2$ is selected from the group consisting of monocyclic aryl and —$CH_2$—C≡CH, (C)

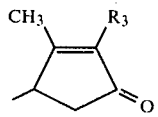

wherein $R_3$ is an aliphatic of 2 to 6 carbon atoms containing at least one carbon-carbon unsaturation, (D)

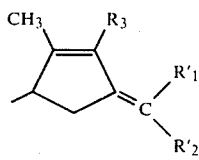

wherein $R_1'$ and $R_2'$ are individually selected from the group consisting of hydrogen, halogen, alkyl of 1 to 6 carbon atoms, aryl of 6 to 10 carbon atoms, alkoxycarbonyl of 2 to 5 carbon atoms and cyano and $R_3$ has the above definition, (E)

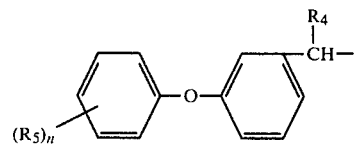

wherein $R_4$ is selected from the group consisting of hydrogen, —CN, —$CH_3$, —$CONH_2$, —$CSNH_2$ and —C≡CH, $R_5$ is selected from the group consisting of chlorine and —$CH_3$ and n is 0,1 or 2, (F) α-cyano-3-phenoxy-benzyl, (G) α-cyano-3-pyridiny-benzyl and (H)

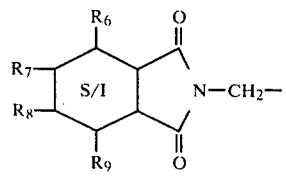

wherein $R_6$, $R_7$, $R_8$ and $R_9$ are individually selected from the group consisting of hydrogen, chlorine, and —$CH_3$ and S/I indicates the ring may be aromatic or dihydro or tetrahydro.

2. A compound of claim 1 wherein the acid moiety has the 1R, cis or 1R, trans structure.

3. A compound of claim 1 or 2 wherein $X_1$ and $X_2$ are the same and are selected from the group consisting of bromine and chlorine.

4. A compound of claim 1 wherein A is α-cyano-3-phenoxy-benzyl.

5. A compound of claim 1 wherein A is 3-allyl-2-methyl-4-oxo-cyclopent-2-en-1-yl.

6. A composition for combatting pests of vegetables and warm-blooded animals comprising a pesticidally effective amount of at least one compound of claim 1 and an inert carrier.

7. An insecticidal composition comprising an insecticidally effective amount of at least one compound of claim 1 and an inert carrier.

8. A composition of claim 7 wherein the acid moiety has the 1R, cis or 1R, trans structure.

9. A composition of claim 7 wherein $X_1$ and $X_2$ are the same and are selected from the group consisting of bromine and chlorine.

10. A composition of claim 7 wherein A is α-cyano-3-phenoxy-benzyl.

11. A composition of claim 7 wherein A is 3-allyl-2-ethyl-4-oxo-cyclopent-2-en-1-yl.

12. A method of combatting insects comprising contacting insects with an insecticidally effective amount of at least one compound of claim 1.

13. A method of claim 12 wherein the acid moiety has the 1R,cis or 1R,trans structure.

14. A method of claim 12 wherein $X_1$ and $X_2$ are the same and are selected from the group consisting of bromine and chlorine.

15. A method of claim 12 wherein A is α-cyano-3-phenoxy-benzyl.

16. A method of claim 12 wherein A is 3-allyl-2-methyl-4-oxo-cyclopent-2-en-1-yl.

* * * * *

UNITED STATES PATENT AND TRADEMARK OFFICE
CERTIFICATE OF CORRECTION

PATENT NO. : 4,401,673

DATED : August 30, 1983

INVENTOR(S) : Jacques Martel et al.

It is certified that error appears in the above-identified patent and that said Letters Patent is hereby corrected as shown below:

Title page [57], third line of Abstract after Formula I, before "(B)" insert
-- with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy, benzyl and halogen; --

Title page [57], line 2 of column 2, before "aryl" insert -- monocyclic --.

Column 3, formula IV: The portion which reads

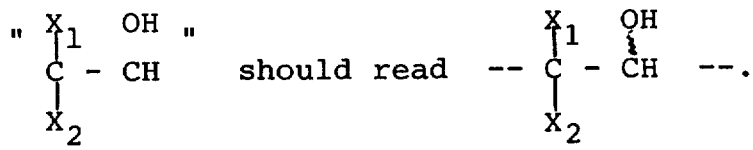

Column 3, formula V: The portion which reads

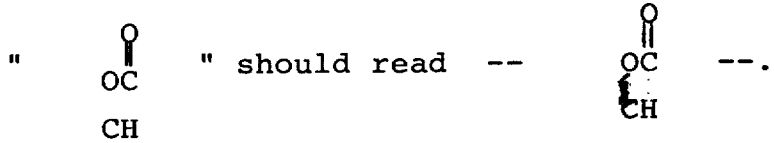

Column 5, line 19: "namatocidal" should be -- nematocidal --.

UNITED STATES PATENT AND TRADEMARK OFFICE
CERTIFICATE OF CORRECTION

PATENT NO. : 4,401,673
DATED : August 30, 1983
INVENTOR(S) : Jacques Martel et al.

It is certified that error appears in the above-identified patent and that said Letters Patent is hereby corrected as shown below:

Column 7, line 10: "(4,40,4',4'-trichloro-" should read
    -- (4',4',4'-trichloro- --.
Column 11, line 40: "6.33 ppm" should read -- 6.3 ppm --.
Column 12, line 48: "or" should read -- of --.
Column 13, line 16: "+116°±1°" should read -- +16°±1° --.

Signed and Sealed this

Tenth Day of July 1984

[SEAL]

Attest:

GERALD J. MOSSINGHOFF

Attesting Officer     Commissioner of Patents and Trademarks

Notice of Adverse Decision in Interference

In Interference No. 101,383, involving Patent No. 4,401,673, J. Martel, J. Tessier and P. Girault, PESTICIDAL 3-(BUTA-1',3'-DIENYL)-CYCLOPROPANE-1-CARBOXYLIC ACID ESTERS, final judgment adverse to the patentees was rendered Aug. 29, 1985, as to claims 1–16.

[*Official Gazette February 11, 1986.*]